United States Patent
Palmer et al.

(10) Patent No.: US 10,130,358 B2
(45) Date of Patent: *Nov. 20, 2018

(54) DEVICES FOR CONTROLLING THE UNLOADING OF SUPERELASTIC AND SHAPE MEMORY ORTHOPEDIC IMPLANTS

(71) Applicant: Arthrex, Inc., Naples, FL (US)

(72) Inventors: Matthew Palmer, Cambridge, MA (US); Matthew Fonte, Concord, MA (US); Robert Devaney, Auburndale, MA (US)

(73) Assignee: Arthrex, Inc., Naples, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/288,108

(22) Filed: Oct. 7, 2016

(65) Prior Publication Data

US 2017/0100163 A1 Apr. 13, 2017

Related U.S. Application Data

(60) Provisional application No. 62/238,472, filed on Oct. 7, 2015.

(51) Int. Cl.
| | | |
|---|---|---|
| *A61B 17/064* | (2006.01) | |
| *A61B 17/68* | (2006.01) | |
| *A61B 17/72* | (2006.01) | |
| *A61B 17/80* | (2006.01) | |
| *A61B 17/86* | (2006.01) | |
| *A61B 17/068* | (2006.01) | |
| *A61B 17/00* | (2006.01) | |

(52) U.S. Cl.
CPC ...... *A61B 17/0642* (2013.01); *A61B 17/0684* (2013.01); *A61B 17/7225* (2013.01); *A61B 17/7291* (2013.01); *A61B 17/8004* (2013.01); *A61B 17/808* (2013.01); *A61B 17/863* (2013.01); *A61B 17/866* (2013.01); *A61B 2017/00867* (2013.01)

(58) Field of Classification Search
CPC . A61B 17/68; A61B 17/0642; A61B 17/7225; A61B 17/8004; A61B 17/866; A61B 17/8872; A61B 17/808; A61B 17/1728; A61B 17/80; A61B 17/8085; A61B 2017/90; A61B 2017/0645; A61B 2017/00867
USPC .............. 606/62–68, 246–279, 300–328
See application file for complete search history.

(56) References Cited

U.S. PATENT DOCUMENTS

| | | | |
|---|---|---|---|
| 6,093,188 A | * | 7/2000 | Murray .............. A61B 17/8004 606/282 |
| 6,325,805 B1 | | 12/2001 | Ogilvie et al. |
| 6,607,530 B1 | | 8/2003 | Carl et al. |
| 6,626,937 B1 | | 9/2003 | Cox |
| 6,656,181 B2 | | 12/2003 | Dixon et al. |
| 6,773,437 B2 | | 8/2004 | Ogilvie et al. |
| 7,172,593 B2 | | 2/2007 | Trieu et al. |

(Continued)

*Primary Examiner* — Pedro Philogene
(74) *Attorney, Agent, or Firm* — Carlson, Gaskey & Olds, P.C.

(57) ABSTRACT

This disclosure provides novel devices for controlling the unloading stress and recoverable strain of Nitinol devices and/or other shape memory material devices. The devices may be used to bring bone fragments into close proximity with each other, generate a compressive load between the bone fragments, and maintain that compressive load between the bone fragments while healing occurs.

13 Claims, 11 Drawing Sheets

(56) References Cited

U.S. PATENT DOCUMENTS

| | | | |
|---|---|---|---|
| 7,309,340 B2 | 12/2007 | Fallin et al. | |
| 7,479,143 B2 | 1/2009 | Suh et al. | |
| 7,618,441 B2 | 11/2009 | Groiso | |
| 7,655,009 B2 | 2/2010 | Grusin | |
| 7,699,879 B2 | 4/2010 | Sherman et al. | |
| 7,763,056 B2 | 7/2010 | Dalton | |
| 7,771,457 B2 | 8/2010 | Kay et al. | |
| 7,875,070 B2 | 1/2011 | Molaei | |
| 7,976,648 B1 | 7/2011 | Boylan et al. | |
| 7,985,222 B2 | 7/2011 | Gall et al. | |
| 7,993,380 B2 | 8/2011 | Hawkes | |
| 8,048,134 B2 * | 11/2011 | Partin | A61B 17/7225 606/301 |
| 8,062,378 B2 | 11/2011 | Fonte | |
| 8,080,044 B2 | 12/2011 | Biedermann et al. | |
| 8,118,952 B2 | 2/2012 | Gall et al. | |
| 8,216,398 B2 | 7/2012 | Bledsoe et al. | |
| 8,257,404 B2 | 9/2012 | Hack | |
| 8,262,659 B2 | 9/2012 | Ryan et al. | |
| 8,394,097 B2 | 3/2013 | Peyrot et al. | |
| 8,419,797 B2 | 4/2013 | Biedermann et al. | |
| 8,425,588 B2 | 4/2013 | Molaei | |
| 8,439,916 B2 | 5/2013 | Coati et al. | |
| 8,460,293 B2 | 6/2013 | Coati et al. | |
| 8,475,457 B2 | 7/2013 | Shano | |
| 8,584,853 B2 | 11/2013 | Knight et al. | |
| 8,623,061 B2 | 1/2014 | Quevedo et al. | |
| 8,715,325 B2 | 5/2014 | Weiner et al. | |
| 8,721,646 B2 | 5/2014 | Fox | |
| 8,740,954 B2 | 6/2014 | Ghobrial et al. | |
| 8,784,459 B2 | 7/2014 | Kaufman et al. | |
| 8,808,294 B2 | 8/2014 | Fox et al. | |
| 8,834,483 B2 | 9/2014 | Cheney et al. | |
| 8,858,603 B1 | 10/2014 | Zufelt | |
| 8,864,804 B2 | 10/2014 | Champagne et al. | |
| 8,888,826 B2 | 11/2014 | Kinmon et al. | |
| 8,894,669 B2 | 11/2014 | Nering et al. | |
| 8,998,999 B2 | 4/2015 | Lewis et al. | |
| 9,017,331 B2 | 4/2015 | Fox | |
| 9,044,281 B2 | 6/2015 | Pool et al. | |
| 9,050,153 B2 | 6/2015 | Luxon et al. | |
| 9,056,014 B2 | 6/2015 | McCormick et al. | |
| 9,072,562 B2 | 7/2015 | Weiner et al. | |
| 9,078,718 B2 | 7/2015 | Campbell | |
| 9,095,338 B2 | 8/2015 | Taylor et al. | |
| 9,101,349 B2 | 8/2015 | Knight et al. | |
| 9,119,681 B2 | 9/2015 | Kaufmann et al. | |
| 9,168,147 B2 | 10/2015 | Patterson et al. | |
| 9,204,932 B2 | 12/2015 | Knight et al. | |
| 9,241,738 B2 | 1/2016 | Quevedo et al. | |
| 9,254,350 B2 | 2/2016 | Udipi et al. | |
| 9,265,531 B2 | 2/2016 | Ziolo | |
| 9,282,977 B2 | 3/2016 | Penzimer et al. | |
| 9,308,035 B2 | 4/2016 | Biedermann et al. | |
| 9,326,794 B2 | 5/2016 | Harms et al. | |
| 9,326,804 B2 | 5/2016 | Biedermann et al. | |
| 9,339,268 B2 | 5/2016 | Fox | |
| 9,339,316 B2 | 5/2016 | Hulliger | |
| 9,408,647 B2 | 8/2016 | Cheney | |
| 9,451,955 B2 | 9/2016 | Fox | |
| 9,451,957 B2 | 9/2016 | Fox | |
| 9,861,413 B2 * | 1/2018 | Palmer | A61B 17/864 |
| 2005/0085814 A1 | 4/2005 | Sherman et al. | |
| 2005/0136764 A1 | 6/2005 | Sherman et al. | |
| 2005/0165394 A1 | 7/2005 | Boyce et al. | |
| 2005/0187555 A1 | 8/2005 | Biedermann et al. | |
| 2005/0240190 A1 | 10/2005 | Gall et al. | |
| 2006/0235405 A1 | 10/2006 | Hawkes | |
| 2006/0264954 A1 | 11/2006 | Sweeney | |
| 2007/0198017 A1 | 8/2007 | Tschakaloff et al. | |
| 2008/0039847 A1 | 2/2008 | Piper et al. | |
| 2008/0097443 A1 | 4/2008 | Campbell | |
| 2008/0215097 A1 | 9/2008 | Ensign | |
| 2008/0243264 A1 | 10/2008 | Fonte | |
| 2008/0262629 A1 | 10/2008 | Fonte | |
| 2009/0125071 A1 | 5/2009 | Skinlo et al. | |
| 2009/0164016 A1 | 6/2009 | Georgy et al. | |
| 2009/0198287 A1 * | 8/2009 | Chiu | A61B 17/863 606/301 |
| 2009/0216334 A1 | 8/2009 | Leibel | |
| 2010/0076498 A1 | 3/2010 | Tyber et al. | |
| 2010/0121329 A1 | 5/2010 | Ryan et al. | |
| 2010/0131014 A1 | 5/2010 | Peyrot et al. | |
| 2010/0211115 A1 * | 8/2010 | Tyber | A61B 17/863 606/305 |
| 2010/0241120 A1 | 9/2010 | Bledsoe et al. | |
| 2011/0004255 A1 | 1/2011 | Weiner et al. | |
| 2011/0066190 A1 | 3/2011 | Schaller et al. | |
| 2011/0112579 A1 | 5/2011 | Brazil et al. | |
| 2011/0190776 A1 | 8/2011 | Palmaz | |
| 2012/0123554 A1 | 5/2012 | Fonte | |
| 2012/0172876 A1 | 7/2012 | Coati et al. | |
| 2012/0271363 A1 | 10/2012 | Luxon et al. | |
| 2013/0030437 A1 | 1/2013 | Fox | |
| 2013/0046346 A1 | 2/2013 | Thorwarth et al. | |
| 2013/0060337 A1 | 3/2013 | Petersheim et al. | |
| 2013/0123857 A1 | 5/2013 | Biedermann et al. | |
| 2013/0123925 A1 | 5/2013 | Patterson et al. | |
| 2013/0190817 A1 * | 7/2013 | Bouduban | A61B 17/0401 606/232 |
| 2013/0206815 A1 * | 8/2013 | Fox | A61B 17/0682 227/176.1 |
| 2013/0226241 A1 | 8/2013 | Thompson et al. | |
| 2013/0274814 A1 | 10/2013 | Weiner et al. | |
| 2013/0325074 A1 | 12/2013 | Ziolo | |
| 2014/0014553 A1 | 1/2014 | Knight et al. | |
| 2014/0018809 A1 | 1/2014 | Allen | |
| 2014/0020333 A1 | 1/2014 | Knight et al. | |
| 2014/0024002 A1 | 1/2014 | Knight et al. | |
| 2014/0114311 A1 | 4/2014 | Pool et al. | |
| 2014/0188237 A1 | 7/2014 | McCormick et al. | |
| 2014/0257291 A1 | 9/2014 | Houff | |
| 2014/0257420 A1 | 9/2014 | Fox | |
| 2014/0277516 A1 | 9/2014 | Miller et al. | |
| 2014/0330313 A1 | 11/2014 | Kaufman et al. | |
| 2014/0336651 A1 | 11/2014 | Bouduban et al. | |
| 2014/0336710 A1 | 11/2014 | Georgy | |
| 2014/0358187 A1 * | 12/2014 | Taber | A61B 17/0642 606/86 R |
| 2014/0358247 A1 | 12/2014 | Fox et al. | |
| 2015/0011998 A1 | 1/2015 | McCormick et al. | |
| 2015/0080970 A1 | 3/2015 | Campbell et al. | |
| 2015/0238237 A1 | 8/2015 | Madjarov | |
| 2015/0238238 A1 | 8/2015 | Cheney | |
| 2015/0245859 A1 | 9/2015 | McMillen et al. | |
| 2015/0257804 A1 | 9/2015 | Baynham | |
| 2015/0305789 A1 | 10/2015 | Weiner et al. | |
| 2016/0051284 A1 | 2/2016 | Cronen | |
| 2016/0095638 A1 | 4/2016 | Reimels | |
| 2016/0135808 A1 | 5/2016 | Anderson | |

* cited by examiner

DEVICES FOR CONTROLLING THE UNLOADING OF SUPERELASTIC AND SHAPE MEMORY ORTHOPEDIC IMPLANTS

CROSS-REFERENCE TO RELATED APPLICATIONS

This application claims priority to U.S. Provisional Application No. 62/238,472, which was filed on Oct. 7, 2015, the disclosure of which is incorporated herein by reference in its entirety.

TECHNICAL FIELD

This disclosure relates to approaches for controlling the unloading stress of Nitinol devices, and/or other shape memory material devices, in order to facilitate healing of diseased or damaged tissue. The present disclosure finds particular utility in the field of orthopedics, and specifically as an approach for creating and using devices for reducing fractures and generating and maintaining compression between bone fragments. While the present disclosure has application throughout the body, its utility will sometimes hereinafter be illustrated in the context of providing and using screws, staples, plates, and/or intramedullary devices for the repair of fractured or displaced bone tissue.

BACKGROUND

In the field of orthopedic surgery, it is common to rejoin broken bones. The success of the surgical procedure often depends on the ability to reapproximate the fractured bone, the amount of compression achieved between the bone fragments, and the ability to sustain that compression over a period of time. If the surgeon is unable to bring the bone fragments into close contact, a gap will exist between the bone fragments and the bone tissue will need to first fill that gap before complete healing can take place. Furthermore, gaps between bone fragments that are too large can allow motion to occur between the fragments, disrupting the healing tissue and thus slowing the healing process. Thus, non-unions, mal-unions, and delayed-unions of fractures can occur when the gap between bone fragments is too large. Optimal healing requires that the bone fragments be in close contact with each other, and for a compressive load to be applied and maintained between the bone fragments. Compressive strain between bone fragments has been found to accelerate the healing process in accordance with Wolf's Law.

Broken bones can be rejoined using screws, staples, plates, intramedullary devices, and other devices known in the art. These devices are designed to assist the surgeon with reducing the fracture and creating a compressive load between the bone fragments.

Screws are typically manufactured from either titanium or stainless steel alloys and may be lag screws or headless screws. Lag screws have a distal threaded region and an enlarged head. The head contacts the cortical bone surface and the action of the threaded region reduces the fracture and generates a compressive load. Headless screws typically have a threaded proximal region and a threaded distal region. A differential in the thread pitch of the two regions generates compression across the fracture site. There also exist fully-threaded headless compression screws that have a thread pitch which differs over the length of the single continuous thread.

Staples are formed from a plurality of legs (typically two legs, although sometimes more than two legs may be provided) connected together by a bridge. Staples are typically manufactured from stainless steel alloys, titanium alloys, or Nitinol, a shape memory alloy. The staples are inserted into pre-drilled holes on either side of the fracture site.

Plates are also used to rejoin broken bones. These plates are generally formed from a sheet or ribbon of material having a plurality of holes formed therein. The plates are typically manufactured from either stainless steel alloys or titanium alloys. The plates are placed adjacent to a fracture so that the plate spans the fracture line, and then screws are inserted through the holes in the plate and into the bone fragments on either side of the fracture site to stabilize the bone fragments relative to one another.

Intramedullary devices are often used for fractures of the long bones; however, they are also frequently used in the phalanges, and specifically for the treatment of "hammer toe", which is a deformity of the proximal interphalangeal joint of the second, third, or fourth toe causing the toe to be permanently bent, e.g., bent upwards. Typical intramedullary devices used in the phalanges have opposing ends that are adapted to grip the interior wall of the intramedullary canal. These intramedullary devices are typically made of titanium alloys, stainless steel alloys, Nitinol and/or other materials, e.g., PEEK. The titanium alloy devices and stainless steel alloy devices often have barbs or threaded regions at their opposing ends to grip the interior wall of the intramedullary canal. The Nitinol devices may have a pair of radially-extending "legs" at their opposing ends that expand outward when warmed to body temperature, with the pair of legs at each end of the device being disposed in a common plane.

While the foregoing devices (e.g., screws, staples, plates, and intramedullary devices) are designed to bring the bone fragments into close contact and to generate a compressive load between the bone fragments, the devices do not always succeed in accomplishing this objective. It is widely reported that the compressive load generated by these devices between the bone fragments dissipates rapidly as the bone relaxes and remodels around the device.

Nitinol can be used to improve the functional performance of these devices by utilizing either the shape memory effect of Nitinol or the superelastic properties of Nitinol to pull together the opposing bone fragments; however, the recovery forces and recoverable strain generated by the Nitinol versions of these devices may be too great and may damage bone tissue and thus not provide a means to generate and maintain compression between the bone fragments.

Thus there exists a clinical need for device that can be used to control the unloading stress and recoverable strain of Nitinol devices, and/or other shape memory material devices, so as to allow for devices that are able to bring bone fragments into close proximity with each other, generate a compressive load, and maintain that compressive load for a prolonged period of time while healing occurs without damaging the bone tissue.

SUMMARY

This disclosure provides novel devices for controlling the unloading stress and recoverable strain of Nitinol devices/implants and/or other shape memory material devices/implants. The devices may be used to bring bone fragments into close proximity with each other, generate a compressive load between the bone fragments, and maintain that compressive load between the bone fragments while healing occurs.

In an embodiment, a device is provided for controlling the recoverable strain and compression generated by a Nitinol staple. The device allows the surgeon to control to what extent the legs of the staple are opened to or beyond the parallel state. The more the staple is opened, the more recoverable strain and compression the staple will exert on the bone. This device is also beneficial because it allows the surgeon to control the rate of loading the compression onto the bone, and also provides a feedback for the surgeon to feel how much compression the bone is experiencing.

In another embodiment, a device is provided for controlling the recoverable strain and compression generated by a Nitinol compression screw. The Nitinol compression screw is elongated and held in the elongated state with an internal retaining pin. It may be provided to the surgeon with the screw stretched to the maximum (~8%). The surgeon can partially withdraw the internal retaining pin to decrease the compressive force and recoverable strain the screw will exert on the bone following implantation. The more the internal retaining pin is removed, the less recoverable stress and strain the screw will exert. This is beneficial because it allows the surgeon to have better control of the device, and may be especially beneficial for the treatment of low density bone fractures.

In another embodiment, a device is provided for controlling the recoverable strain and compression generated by a Nitinol compression plate. The Nitinol compression plate is elongated and held in the elongated state with a delivery device. It may be provided to the surgeon with the plate fully elongated. The surgeon can use the delivery device to allow for partial stress/strain recovery of the device prior to implantation. This is beneficial because it allows the surgeon to have better control of the device, and may be especially beneficial for the treatment of low density bone fractures.

In yet another embodiment, a device is provided for controlling the recoverable strain and compression generated by a Nitinol intramedullary implant. The Nitinol intramedullary implant is provided in an elongated state with an internal retaining pin. The surgeon can partially withdraw the internal retaining pin to decrease the compressive force and recoverable strain the intramedullary implant will exert on the bone following implantation. The more the internal retaining pin is removed, the less recoverable stress and strain the intramedullary implant will exert. This is beneficial because it allows the surgeon to have better control of the device, and may be especially beneficial for the treatment of low density bone fractures.

BRIEF DESCRIPTION OF THE DRAWINGS

The various features and advantages of this disclosure will become apparent to those skilled in the art from the following detailed description. The drawings that accompany the detailed description can be briefly described as follows.

DETAILED DESCRIPTION

Figure 1:
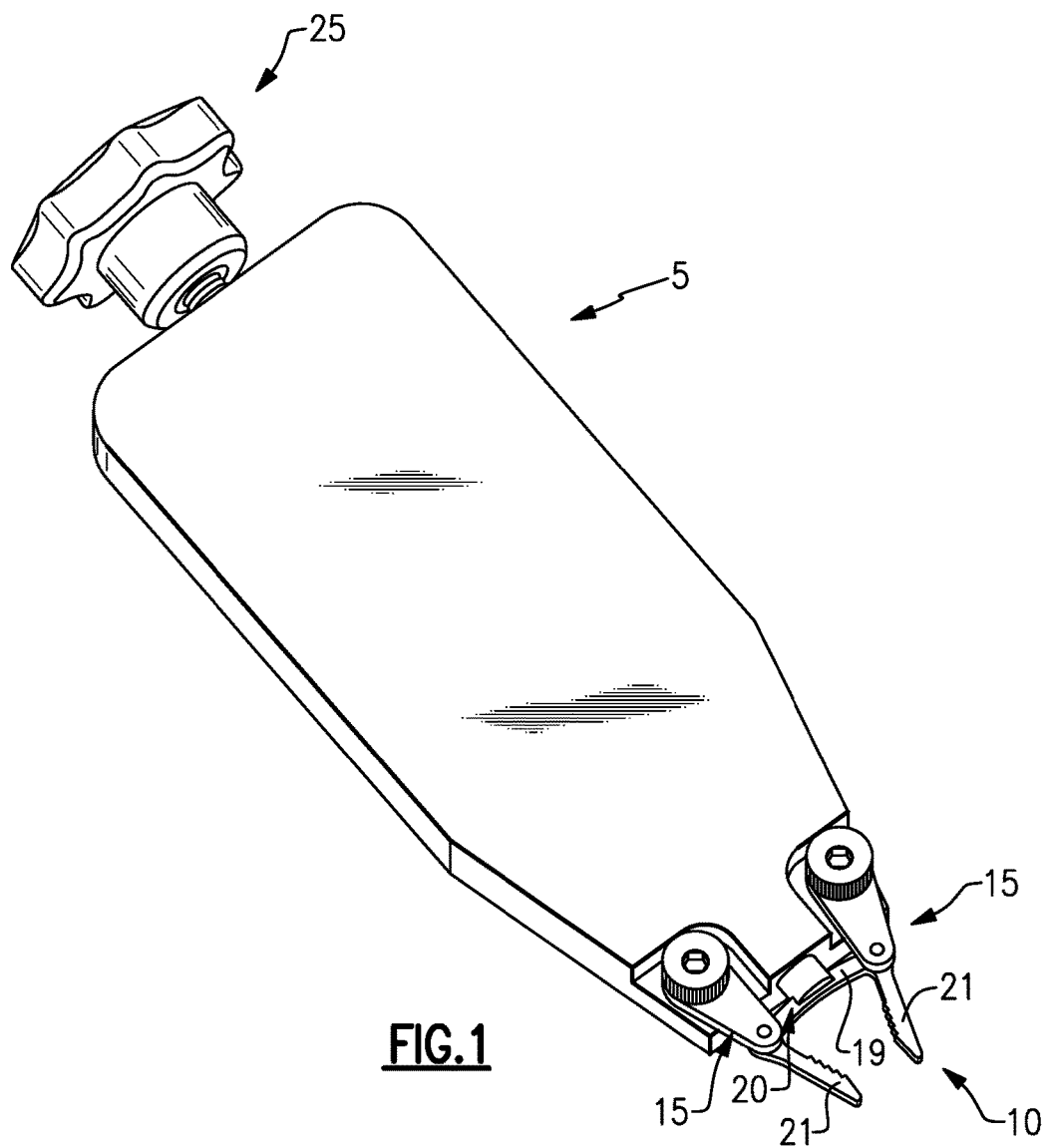
FIGS. 1, 2, 3, and 4 schematically illustrate a staple delivery device that can be used to control the recoverable strain and compressive force generated by the staple.
Figure 2:
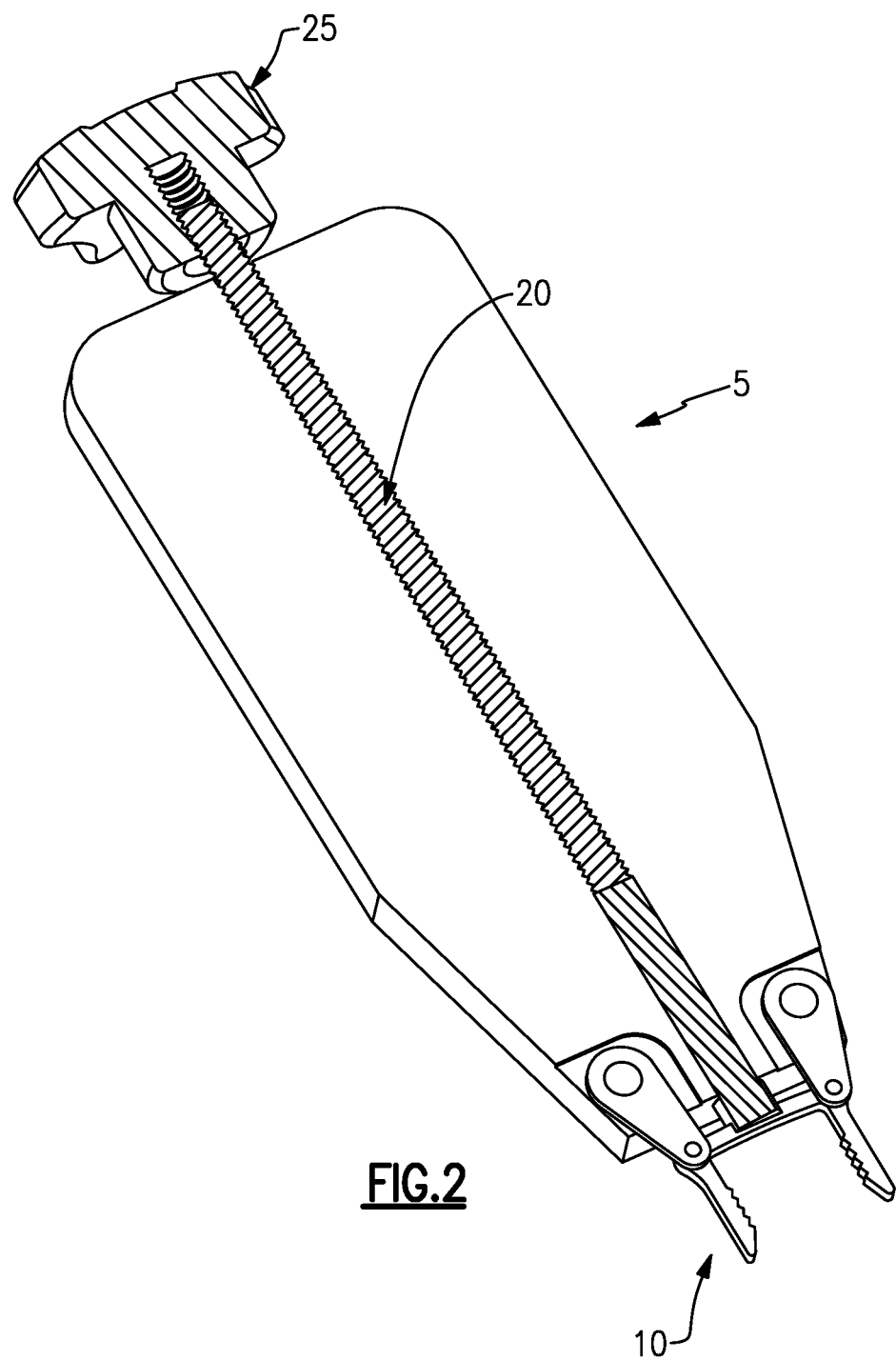
Figure 3:
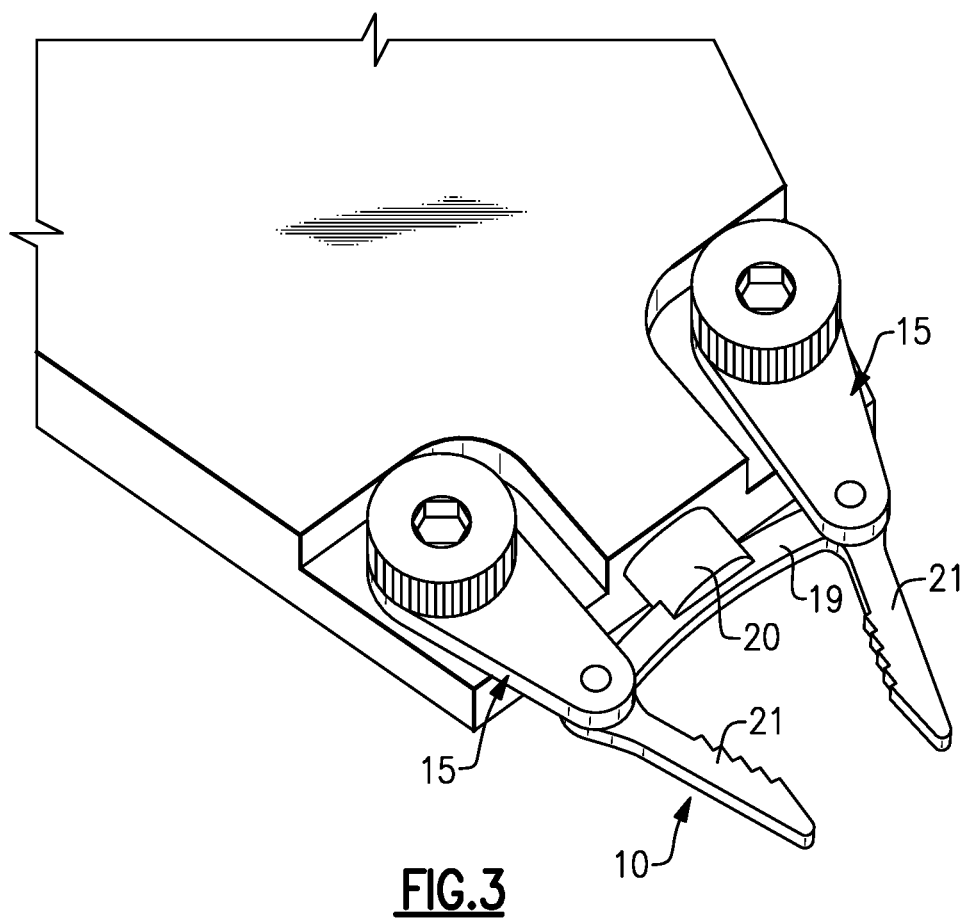
Figure 4:
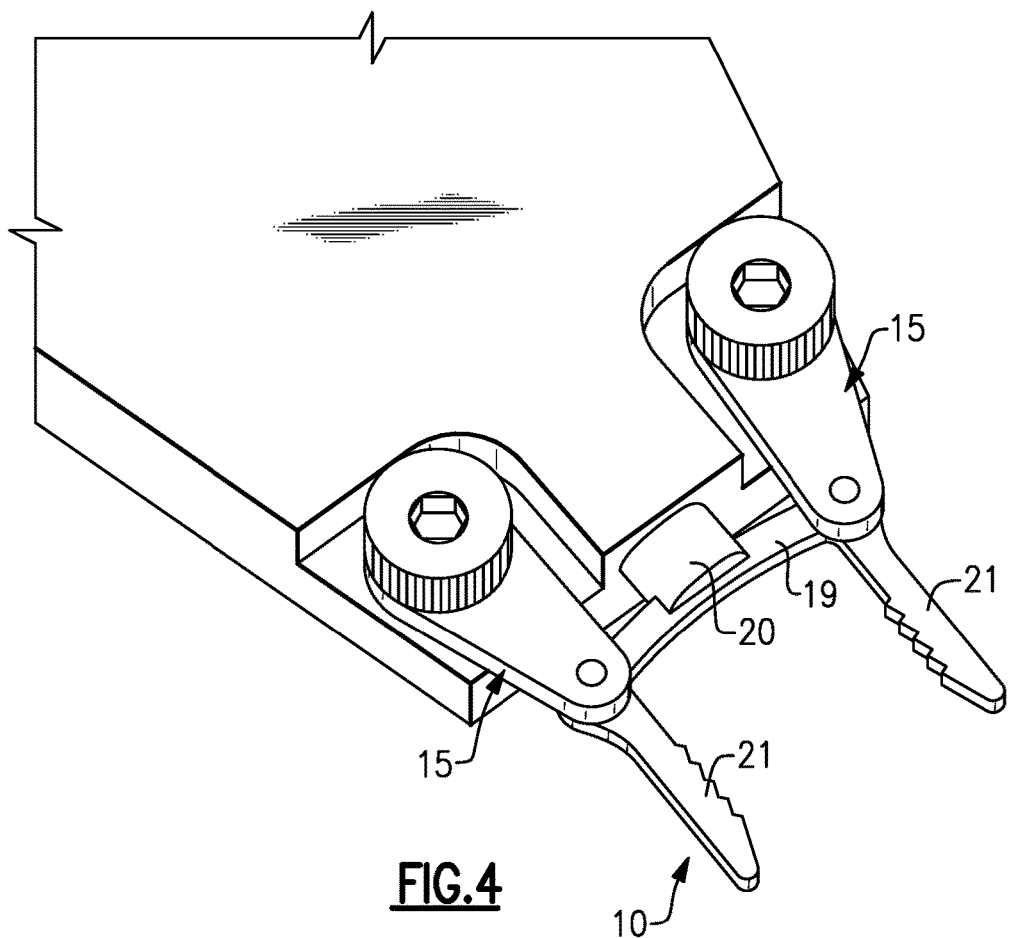

A method for controlling an unloading stress of an orthopedic implant according to an exemplary aspect of this disclosure includes, inter alia, positioning an implant made of a shape memory material in a deformed state to generate a stress level and recoverable strain within the implant, holding the implant in the deformed state with a retaining mechanism, and adjusting the retaining mechanism to control a level of deformation of the implant and alter the stress level and recoverable strain of the implant.

In a further embodiment, an implant is a compression screw.

In a further embodiment, a compression screw is made of Nitinol.

In a further embodiment, an implant is a compression staple.

In a further embodiment, a compression screw is made of Nitinol.

In a further embodiment, an implant is a compression plate.

In a further embodiment, a compression plate is made of Nitinol.

In a further embodiment, an implant is an intramedullary implant.

In a further embodiment, an intramedullary implant is made of Nitinol.

In a further embodiment, positioning an implant in a deformed state includes using superelastic or shape memory properties of the implant.

In a further embodiment, a retaining mechanism is a delivery device.

In a further embodiment, a delivery device includes a plunger.

In a further embodiment, a retaining mechanism is an internal retaining pin.

In a further embodiment, adjusting a retaining mechanism includes advancing a plunger to spread legs of an implant apart.

In a further embodiment, adjusting a retaining mechanism includes partially unscrewing an internal retaining pin from a central hollow region of an implant.

In a further embodiment, adjusting a retaining mechanism includes moving a restraining clip to change an amount that a central bridge of an implant bows outward.

In a further embodiment, at least a portion of an implant is reversibly stretched prior to holding the implant with a retaining mechanism.

In a further embodiment, an unloading stress of an implant is controlled with a retaining mechanism during implantation of the implant into bone.

A method according to another exemplary aspect of this disclosure includes, inter alia, positioning an implant made of a shape memory material in a deformed state to generate a stress level and recoverable strain within the implant, adjusting a level of deformation of the implant to alter the stress level and recoverable strain of the implant, and implanting the implant into bone, wherein the implant exerts a compressive load on the bone that is proportional to the stress level and recoverable strain generated in the implant while adjusting the level of deformation Referring first to FIGS. 1-4, there is shown a novel device for controlling the recoverable strain and compressive force generated by a compression staple 10 made of a shape memory material such as Nitinol. The compression staple 10 is an exemplary type of orthopedic implant. A delivery device 5 (i.e., a retaining mechanism) holds the compression staple 10 on a pair of pin plates 15. A plunger 20 is connected to a knob 25. Turning the knob 25 causes the plunger 20 to advance and contact a bridge 19 of the compression staple 10, and this contact spreads the legs 21 of compression staple 10 apart. The more that the knob 25 is advanced, the more the compression staple 10 legs 21 open, and thus the more compressive force and recoverable strain the compression staple 10 is capable of. The delivery device 5 also provides the surgeon with feedback as to how much compression the staple is going to exert. The more the knob 25 is turned, the more torque that is required. The torque required to turn the knob 25 is related to and may be directly proportional to the compressive force and recoverable strain the compression staple 10 will exert upon implantation into bone.

Figure 5:
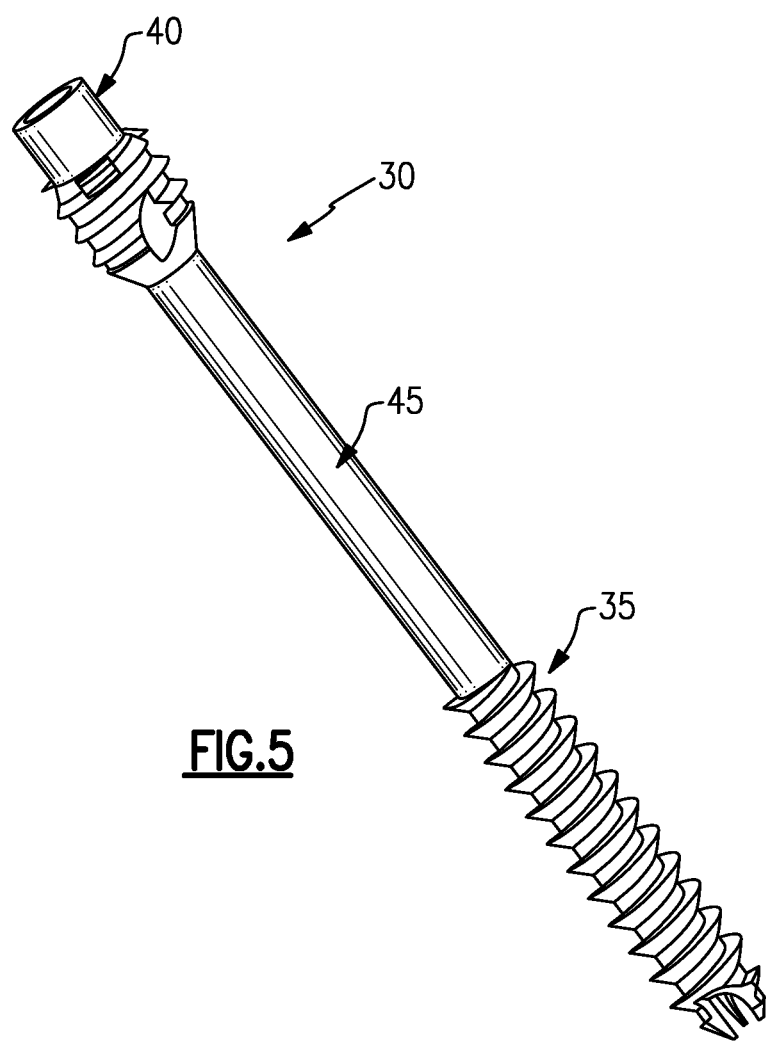
FIGS. 5 and 6 schematically illustrate a compression screw system that has an internal retaining pin that can be used to control the recoverable strain and compressive force generated by the screw.
Figure 6:
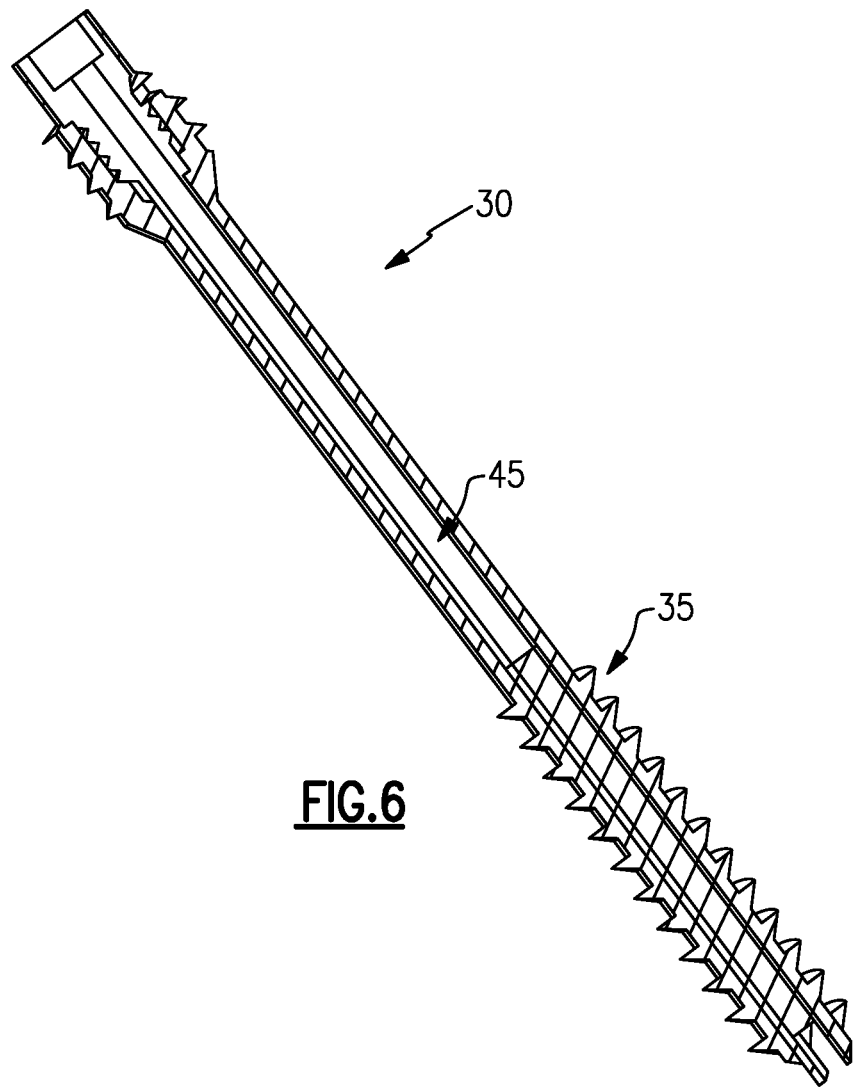

Referring next to FIGS. 5 and 6, there is shown a compression screw system 30. The compression screw system 30 is another exemplary type of orthopedic implant. The compression screw system 30 includes compression screw 35 made of a shape memory material, such as Nitinol, and an internal retaining pin 40 (i.e., a retaining mechanism). During manufacturing, a central hollow region 45 of the compressions screw 35 is reversibly stretched. The internal retaining pin 40 is inserted into the compression screw 35 and keeps the compression screw 35 stretched. Prior to implantation, the surgeon can partially unthread the internal retaining pin 40. This will allow for partial recovery of the elongation of the compression screw 35. The more that the internal retaining pin 40 is unscrewed, the less compressive force and recoverable strain the compression screw 35 will exert when the internal retaining pin 40 is fully removed following implantation.

Figure 7:
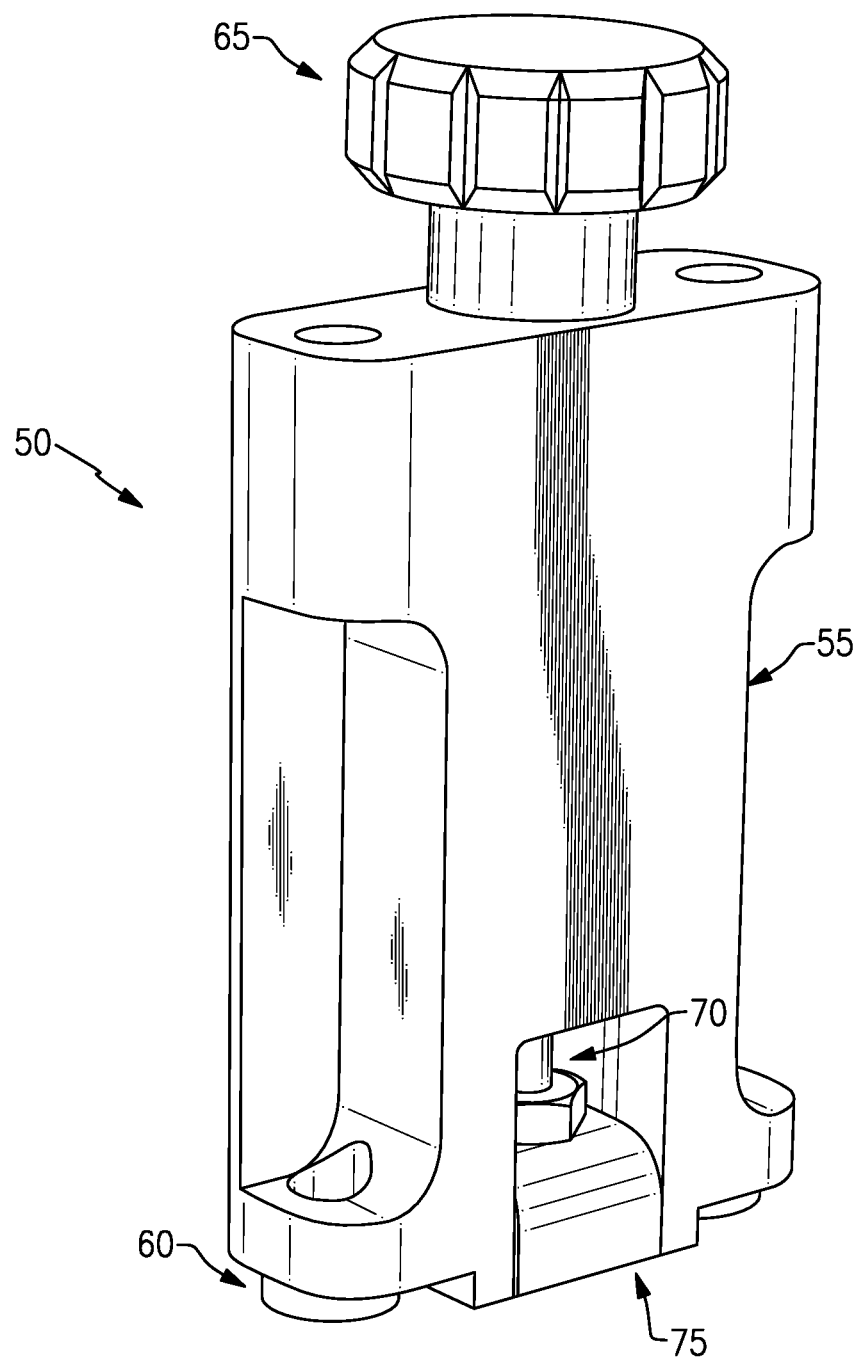
FIGS. 7, 8, and 9 schematically illustrate a compression plate delivery device that has the ability to be adjusted by the surgeon to control the recoverable strain and compressive force generate by the compression plate.
Figure 8:
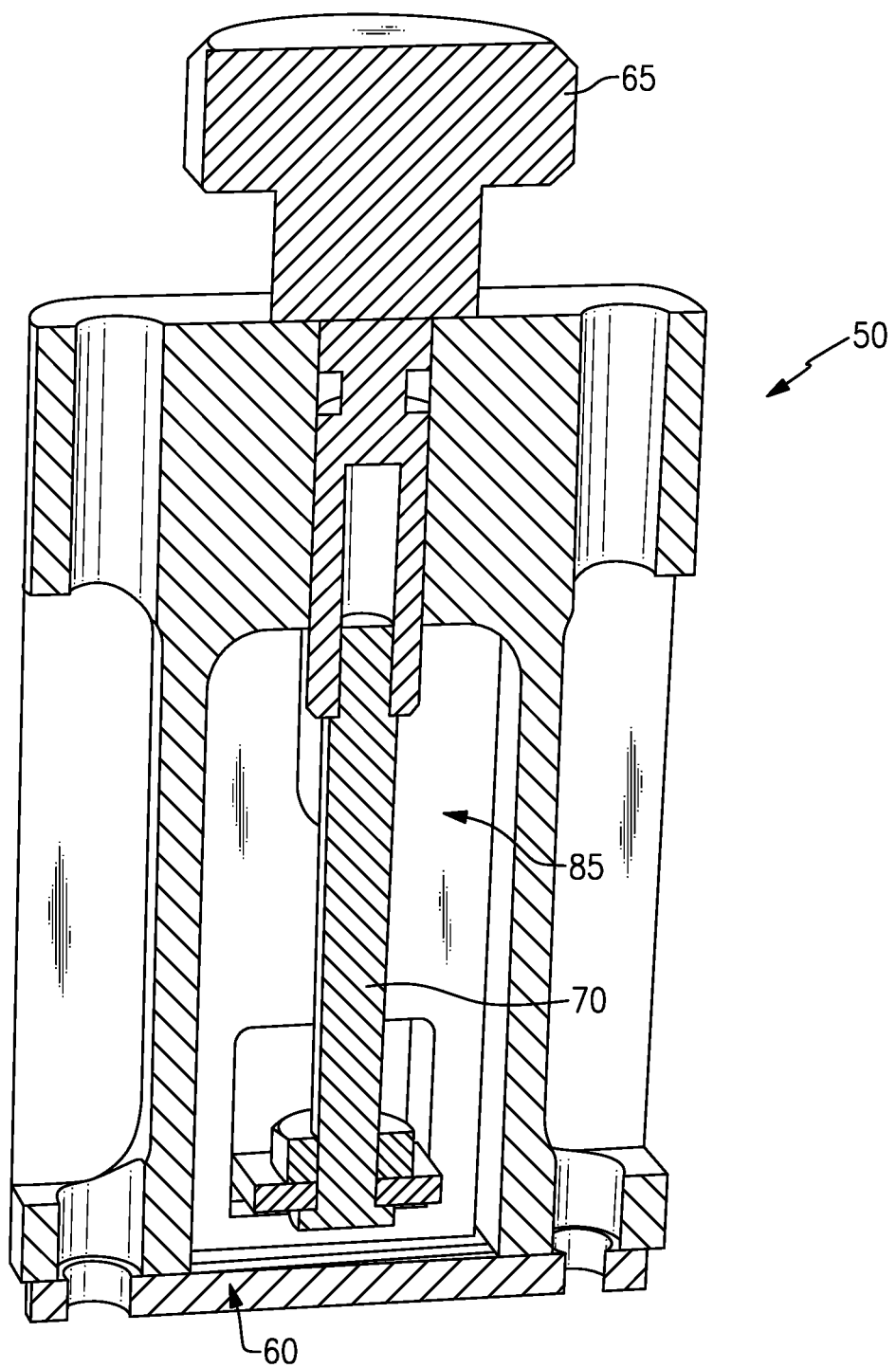
Figure 9:
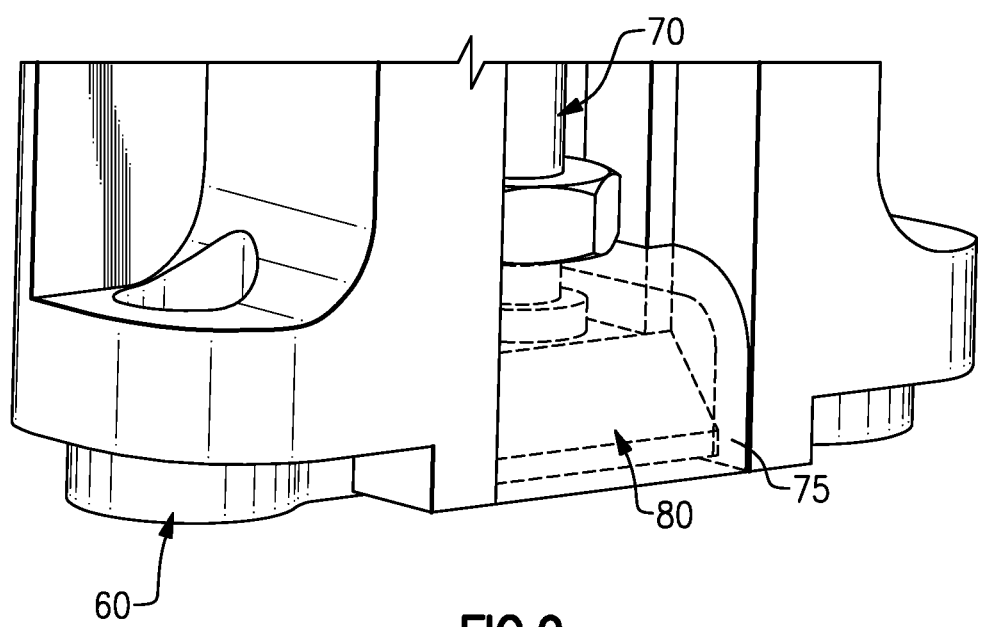

FIGS. 7, 8, and 9 illustrate a compression plate system 50. The compression plate system 50 is yet another exemplary type of orthopedic implant. The compression plate system 50 includes a delivery device 55 (i.e., a retaining mechanism) and a compression plate 60 made of a shape memory material, such as Nitinol. The delivery device 55 has a knob 65 connected to a plunger 70 and a restraining clip 75. Turning the knob 65 clockwise causes the restraining clip 75 to translate toward the knob 65. As the restraining clip 75 translates upward, it rides on a chamfer 80 (see FIG. 9). A cover 85 (see FIG. 8) of the delivery device 55 is hinged so as to allow the cover 85 to articulate open as the restraining clip 75 travels up the chamfer 80. As this happens, a central bridge of the compression plate 60 bows outward. This reduces the recoverable strain and compressive force that compression plate 60 will generate following implantation.

Figure 10:
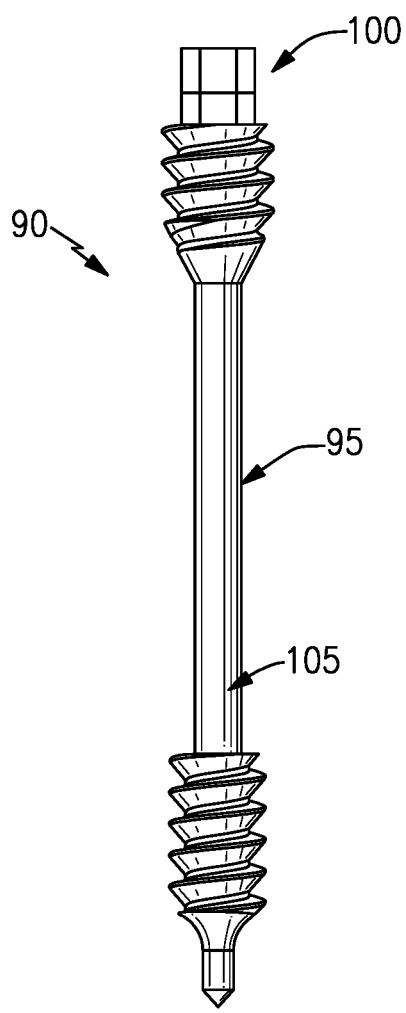
FIGS. 10 and 11 schematically illustrate an intramedullary implant system that has an internal retaining pin that can be used to control the recoverable strain and compressive force generated by the intramedullary implant.
Figure 11:
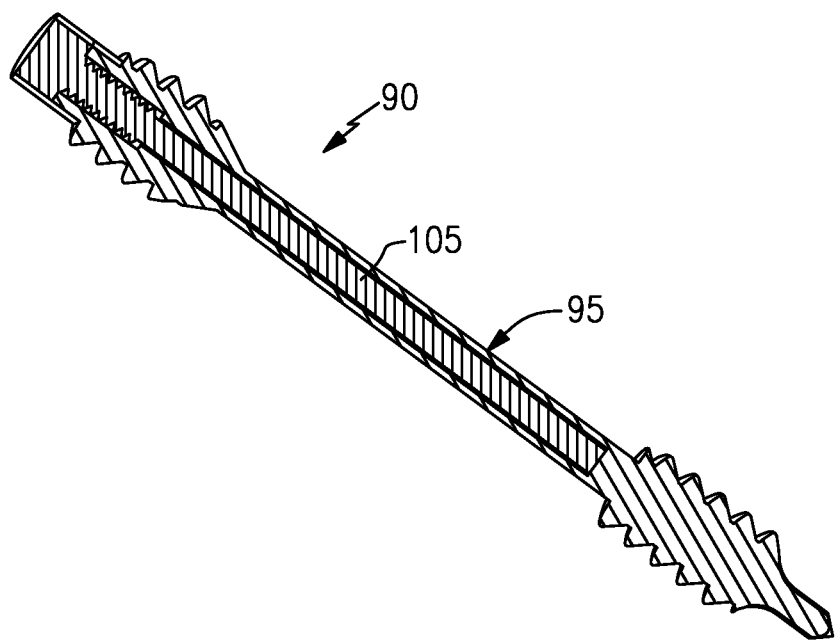

Referring now to FIGS. 10 and 11, there is shown an intramedullary implant system 90. The intramedullary implant system 90 is yet another exemplary type of orthopedic implant. The intramedullary implant system 90 includes an intramedullary implant 95 made of a shape memory material (e.g., Nitinol) and an internal retaining pin 100 (i.e., a retaining mechanism). During manufacturing, a central hollow region 105 of the intramedullary implant 95 is reversibly stretched. The internal retaining pin 100 is inserted into the intramedullary implant 95 and keeps the implant stretched. Prior to implantation, the surgeon can partially unthread the internal retaining pin 100. This will allow for partial recovery of the elongation of the intramedullary implant 95. The more that internal retaining pin 100 is unscrewed, the less compressive force and recoverable strain the intramedullary implant 95 will exert when the internal retaining pin 100 is fully removed following implantation.

The foregoing description shall be interpreted as illustrative and not in any limiting sense. A worker of ordinary skill in the art would recognize that certain modifications could come within the scope of this disclosure. For these reasons, the following claims should be studied to determine the true scope and content of this disclosure.

What is claimed is:

1. A method for controlling an unloading stress of an orthopedic implant comprising:
   deforming a shape memory material implant to generate a stress level and recoverable strain within the implant;
   holding the implant in the deformed state with a retaining mechanism, wherein the retaining mechanism is configured to allow adjustment of stress and recoverable strain of the implant; and
   inserting the deformed implant into pre-drilled holes in bone.

2. The method of claim 1, further comprising adjusting the retaining mechanism to alter the stress level and recoverable strain.

3. The method of claim 1, wherein the shape memory material is nitinol.

4. The method of claim 3, wherein the implant is a staple.

5. The method of claim 3, wherein the implant is a compression screw.

6. The method of claim 3, wherein the implant is a compression plate.

7. The method of claim 3, wherein the implant is an intramedullary implant.

8. The method of claim 3 further comprising adjusting the retaining mechanism to control the extent of staple legs opening to or beyond a parallel state.

9. The method of claim 1, wherein the retaining mechanism comprises an internal retaining pin.

10. The method of claim 1, wherein at least a portion of the implant is reversibly stretched prior to holding the implant with the retaining mechanism.

11. A method for controlling an unloading stress of an orthopedic implant comprising:
    deforming a shape memory material implant to generate a stress level and recoverable strain within the implant;
    holding the implant in the deformed state with a retaining mechanism;
    adjusting the retaining mechanism to alter the stress level and recoverable strain; and
    inserting the deformed implant into pre-drilled holes in bone.

12. The method of claim 11, wherein the shape memory material is nitinol.

13. The method of claim 11, wherein the implant is selected from the group consisting of a staple, a compression screw, an intramedullary implant, and a compression plate.

* * * * *